US006517500B2

(12) United States Patent
Ichikawa

(10) Patent No.: US 6,517,500 B2
(45) Date of Patent: Feb. 11, 2003

(54) MASSAGER HAVING TREATMENT MEMBERS ADAPTED TO BE MOVED IN AN ARC SHAPE

(75) Inventor: Hiromitsu Ichikawa, Odawara (JP)

(73) Assignee: Toshiba Tech Kabushiki Kaisha

( * ) Notice: Subject to any disclaimer, the term of this patent is extended or adjusted under 35 U.S.C. 154(b) by 0 days.

(21) Appl. No.: 09/739,473

(22) Filed: Dec. 18, 2000

(65) Prior Publication Data

US 2001/0004679 A1 Jun. 21, 2001

(30) Foreign Application Priority Data

Dec. 20, 1999 (JP) ........................................ 11-361206

(51) Int. Cl.[7] ................................................ A61M 7/00

(52) U.S. Cl. .......................... 601/98; 601/97; 601/101; 601/148

(58) Field of Search ................................ 601/133, 134, 601/97–103, 112, 115–116, 148

(56) References Cited

U.S. PATENT DOCUMENTS

| | | | | |
|---|---|---|---|---|
| 4,003,374 A | * | 1/1977 | Mizrachy | 128/48 |
| 4,009,710 A | | 3/1977 | Inada | |
| 5,179,940 A | | 1/1993 | Barreiro | |
| 5,741,218 A | * | 4/1998 | Fujii | 601/90 |
| 6,056,707 A | * | 5/2000 | Hayashi | 601/99 |
| 6,117,094 A | | 9/2000 | Fujii | |
| 6,200,282 B1 | * | 3/2001 | Furuie et al. | 601/98 |

FOREIGN PATENT DOCUMENTS

| | | |
|---|---|---|
| DE | 296 02 938 | 7/1996 |
| DE | 198 08 950 | 9/1998 |
| EP | 809 993 | 12/1997 |
| JP | 56-155832 | 4/1980 |
| JP | 9-327492 | 12/1997 |
| JP | 11-235369 | 8/1999 |
| JP | 2000-93474 | 4/2000 |
| TW | 370457 | 9/1999 |

OTHER PUBLICATIONS

Taiwanese Official Action in Counterpart Taiwanese Patent Application No. 89126283, and English Translation Thereof.

Patent Abstracts of Japan, vol. 1998, No. 11, Sep. 30, 1998 & JP 10 155855A (TEC Corp), Jun. 16, 1998.

Patent Abstracts of Japan, vol. 1999, No. 13, Nov. 30, 1999 & JP 11 235369A (Toshiba TEC Corp), Aug. 31, 1999.

* cited by examiner

*Primary Examiner*—Justine R. Yu
(74) *Attorney, Agent, or Firm*—Frishauf, Holtz, Goodman & Chick, P.C.

(57) ABSTRACT

A chair-type massager is provided which includes a chair body for use as a support member for supporting a user's body and a massage apparatus located in a seat back of the chair body. The massage apparatus includes a base member and a pair of massage units, right and left, provided on the base member. Each massage unit has a movable element. The movable element is provided with a tilt member. A treatment member is attached to the tilt member. The tilt member is driven by means of an airbag. The movable element is rotated around a shaft by means of a motor so that the treatment member can move along a curved surface of the user's body.

6 Claims, 8 Drawing Sheets

MASSAGER HAVING TREATMENT MEMBERS ADAPTED TO BE MOVED IN AN ARC SHAPE

CROSS-REFERENCE TO RELATED APPLICATIONS

This application is based upon and claims the benefit of priority from the prior Japanese Patent Application No. 11-361206, filed Dec. 20, 1999, the entire contents of which are incorporated herein by reference.

BACKGROUND OF THE INVENTION

The present invention relates to a massager with treatment members for massaging a user's body.

Conventionally known are air massagers using airbags that inflate and deflate as they are aerated and deaerated. Also known are massagers that use mechanical drive means to swing pressure members. It is generally known, moreover, that these massagers are chair-type massagers having a seat cushion and a seat back. The chair-type air massagers using the airbags and the chair-type massagers using the mechanically-operated pressure members will hereinafter be referred to simply as massagers, in some cases.

In general, the conventional massagers are designed simply to press a user's body by means of the airbags or the pressure members. The massage effect is known to be able to be effectively enhanced by locally pressing the user's body by means of the pressure members, thereby producing a finger-pressure effect and partially exerting a kneading effect on the user's body. Accordingly, a massager capable of exerting the finger-pressure effect and the kneading effect is being contrived in the field.

In a massager that uses airbags, an example of means for exerting the finger-pressure effect is composed of a pressure member on a swing plate that rocks around a hinge and can be swung by means of an airbag. In some cases, the airbag itself may be provided with the pressure member. On the other hand, a massager is known in which a plurality of pressure members are brought close to or separated from one another by using mechanical means.

The massager that uses airbags may be provided with a known mechanism that can knead the nape of the user's body. In one such mechanism, for example, a pair of swing plates, right and left, rockable around hinges, are opposed to each other in the seat back of a chair-type massager, and a pressure member is provided on each of the swing plates. In the massager of this type, the swing plates are brought close to or separated from each other as the airbags are deflated or inflated. As this is done, the pressure members hold the nape of the neck from both sides, thereby exerting a finger-pressure effect and a kneading effect on it. In the massager having the pressure members that are operated mechanically, the finger-pressure effect and the kneading effect are produced by moving the pressure members toward and away from one another by means of the power of a motor or the like.

Exerting the kneading effect requires a mechanism for partially holding the user's body by means of the pressure members. However, a massager having this mechanism is complicated in construction. And although there are conventional massagers that can knead the nape of the neck, legs, as well as other regions which can be held with ease, there exist no massagers that can hold and knead other parts of the user's body.

Conventionally, moreover, there are massagers that can exert the finger-pressure effect or the kneading effect on the user's body while moving the pressure members in the vertical or horizontal direction of the body. However, there are no existing massagers in which each pressure member is moved along, for example, a curved surface portion of the user's body that ranges from the neck area to the shoulder area as it massages the body. Thus, the conventional massagers should be further improved for a higher massage effect.

BRIEF SUMMARY OF THE INVENTION

Accordingly, the object of the present invention is to provide a massager capable of enhancing the massage effect.

In order to achieve the above object, a massager according to the present invention comprises a support member for supporting a user's body, a base member provided on the support member, and a pair of massage units, right and left, arranged on the base member, each of the massage units including a movable element provided on the base member, a treatment member provided on the movable element, and a moving mechanism for driving the movable element so that the treatment member moves along a part of the user's body in the form of a curved surface.

In the massager of this invention, the treatment member of each of the paired massage units is moved along, for example, a curved surface that ranges from the neck area of the user's body to the shoulder area as it massages the user's body. Thus, a satisfactory massage effect can be obtained.

Preferably, the massager of this invention further comprises a shaft for rockably supporting the movable element so that the treatment member can move along a region of the user's body from the nape area to the shoulder area and a moving mechanism for rocking the movable element around the shaft.

The massager of this invention massages the user's body in a manner such that each movable element is rocked around its shaft, thereby causing each treatment member to move leaving a trace that resembles a curved surface of the user's body ranging from the neck area to the shoulder area or the like. Thus, a satisfactory massage effect can be obtained. Besides, the treatment member can be moved along a path that is similar to the shape of the user's body with use of a simple mechanism that rocks the movable element around the shaft.

Preferably, the massager of this invention further comprises an operating member located on the movable element and provided with the treatment member, hinge means for supporting the proximal portion of the operating member so that the treatment member can move toward and away from the user's body, and an actuator located between the movable element and the operating member and adapted to inflate or deflate when air is supplied thereto or discharged therefrom. In the massager of this invention, the operating member is activated by means of the hinge means and the actuator such as an airbag, whereby the treatment member is moved toward or away from the user's body. In this case, the mechanism for operating the treatment member can be simplified in construction.

In order to achieve the above object, a massager according to the present invention comprises a support member for supporting a user's body, a base member mounted on the support member, a first massage unit provided on the base member, and a second massage unit provided on the base member. The first massage unit includes a first operating member provided on the base member, a first treatment member provided on the operating member, first hinge means for supporting one end portion of the first operating member so that the other end portion of the first operating member can move back and forth, and a first actuator for actuating the first operating member. The second massage unit includes a second operating member provided on the base member, a second treatment member provided on the second operating member, second hinge means for supporting the upper end portion of the second operating member so that the lower end portion of the second operating member can move back and forth, and a second actuator for moving the second operating member forward with respect to the base member.

The massager of this invention can exert a kneading effect in a manner such that the first and second treatment members hold a region of the user's body to be massaged between them when they approach each other. When the first treatment member presses the top portion of the shoulder from above, for example, the second treatment member presses the back portion of the user's body. Thus, a region from the shoulder area to the back region is held between the first and second treatment members. In consequence, a finger-pressure effect and a kneading effect can be exerted on the region from the shoulder area to the back portion, so that a better massage effect can be obtained.

In the massager of this invention, the first massage unit may include a moving mechanism for moving the first treatment member along a region of the user's body from the nape area to the shoulder area, and the second massage unit may include the second treatment member in a position such that the second treatment member can press a back portion of the user's body. In this case, the second treatment member is located substantially in a fixed position with respect to the back portion of the user's body. The first treatment member moves around the second treatment member along a curved surface portion that ranges from the nape area or the neck area to the shoulder area. Thus, a kneading effect and a finger-pressure effect can be exerted on the region from the nape area to the shoulder area, so that the massage effect can be improved further.

In the massager of this invention, the first massage unit may include a movable element provided with the first operating member, a shaft for rockably supporting the movable element so that the first treatment member can move along a region of the user's body from the nape area to the shoulder area, and the moving mechanism for rocking the movable element around the shaft. In this arrangement, the first treatment member can be moved leaving a trace that resembles a curved surface portion ranging from the neck area to the shoulder area by means of the movable element with a simple construction that rocks around the shaft.

In the massager of this invention, the first massage unit may includes the first treatment member normally projecting ahead of the base member, and the second massage unit may includes the second treatment member located in a region such that the second treatment member can press a back portion of the user's body and a recess formed in the base member so that the recess can hold the second treatment member when the back portion is not pressed. In the massager of this invention, the first treatment member projects forward from the base member, so that it can be positioned with ease. Since the second treatment member is held in the recess during the positioning operation, it can be prevented from pushing the back portion and hindering the positioning operation.

In any of the massagers described above, the support member may be a chair body including a seat cushion and a seat back. According to this chair-type massager, the user can be in a sitting position on a chair when he/she is massaged. Thus, the user can be massaged fully relaxed without failing to enjoy the functions and effects of the massager.

In the chair-type massager of this invention, the seat back may be provided with a lift mechanism for vertically moving the base member. According to this arrangement, the elevation of the treatment member can be adjusted in accordance with the constitution or preference of the user to be massaged.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

A massager according to a first embodiment of the present invention will now be described with reference to FIGS. 1 to 9B.

Figure 1:
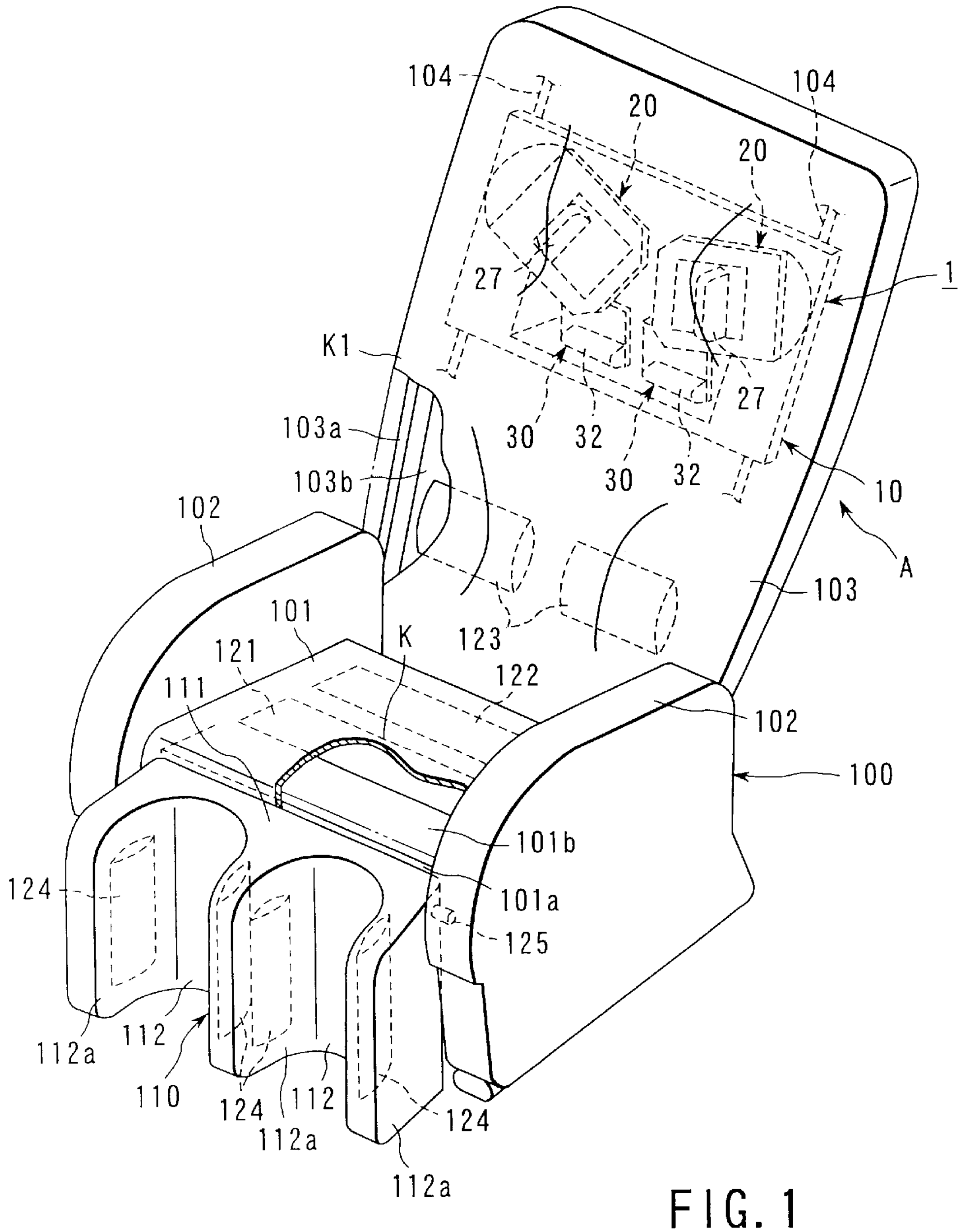
FIG. 1 is a cutaway perspective view showing a chair-type massager according to a first embodiment of the present invention.

A chair-type air massager A shown in FIG. 1 comprises a chair body 100. The chair body 100 includes a seat cushion

101, arm rests 102 arranged individually on the opposite side portions, right and left, of the seat cushion 101, a seat back 103 attached to the rear portion of the seat cushion 101 for reclining motion, etc. The seat back 103 has a massage apparatus 1 (mentioned later) therein. A footrest 110 is attached to the front part of the seat cushion 101.

The seat cushion 101 is provided with an airbag 121 for thighs and an airbag 122 for buttocks. The seat back 103 is provided with the massage apparatus 1 and a pair of airbags 123 for waist. The footrest 110 is provided with airbags 124 for legs. An aeration/deaeration device 50 (shown in FIG. 8, mentioned later) is located under the seat cushion 101.

The seat back 103 includes a frame member 103*a* (only part of which is shown in FIG. 1) and a board 103*b* attached to the member 103*a*. The airbags 123 for waist are located individually in bisymmetrical positions on the board 103*b*. The frame member 103*a* is provided with a pair of guide shafts 104, right and left, which extend vertically. These guide shafts 104 are arranged parallel to each other in the opposite side portions of the seat back 103, individually. The seat back 103 is covered entire by means of a cover member K1 (part of which is broken away in FIG. 1). The cover member K1 conceals the frame member 103*a*, board 103*b*, airbags 123 for waist, massage apparatus 1, guide shafts 104, etc. from the outside.

The seat cushion 101 includes a seat plate 101*a*, a cushion member 101*b* thereon, etc. The airbag 121 for thighs, airbag 122 for buttocks, etc. are arranged in predetermined positions in the cushion member 101*b*. The seat cushion 101 is also covered by means of a cover member K2 (part of which is broken away in FIG. 1). The cover member K2 conceals the airbag 121 for thighs and the airbag 122 for buttocks from the outside.

As shown in FIG. 1, the footrest 110 is provided with a base 111. The base 111 is formed having a pair of grooves 112 with a U-shaped cross section, which extend parallel to each other. The airbags 124 for legs are arranged inside opposite side wall portions 112*a* of the grooves 112, individually. The base 111 is supported on a horizontal shaft 125 for vertical rocking motion with respect to the chair body 100. The shaft 125 is attached to side plates (not shown) that constitute the arm rests 102. The footrest 110 can be vertically rocked by means of a link mechanism or the like, which is activated by means of an actuator, such as an air cylinder, and can be fixed to a desired position.

Figure 8:
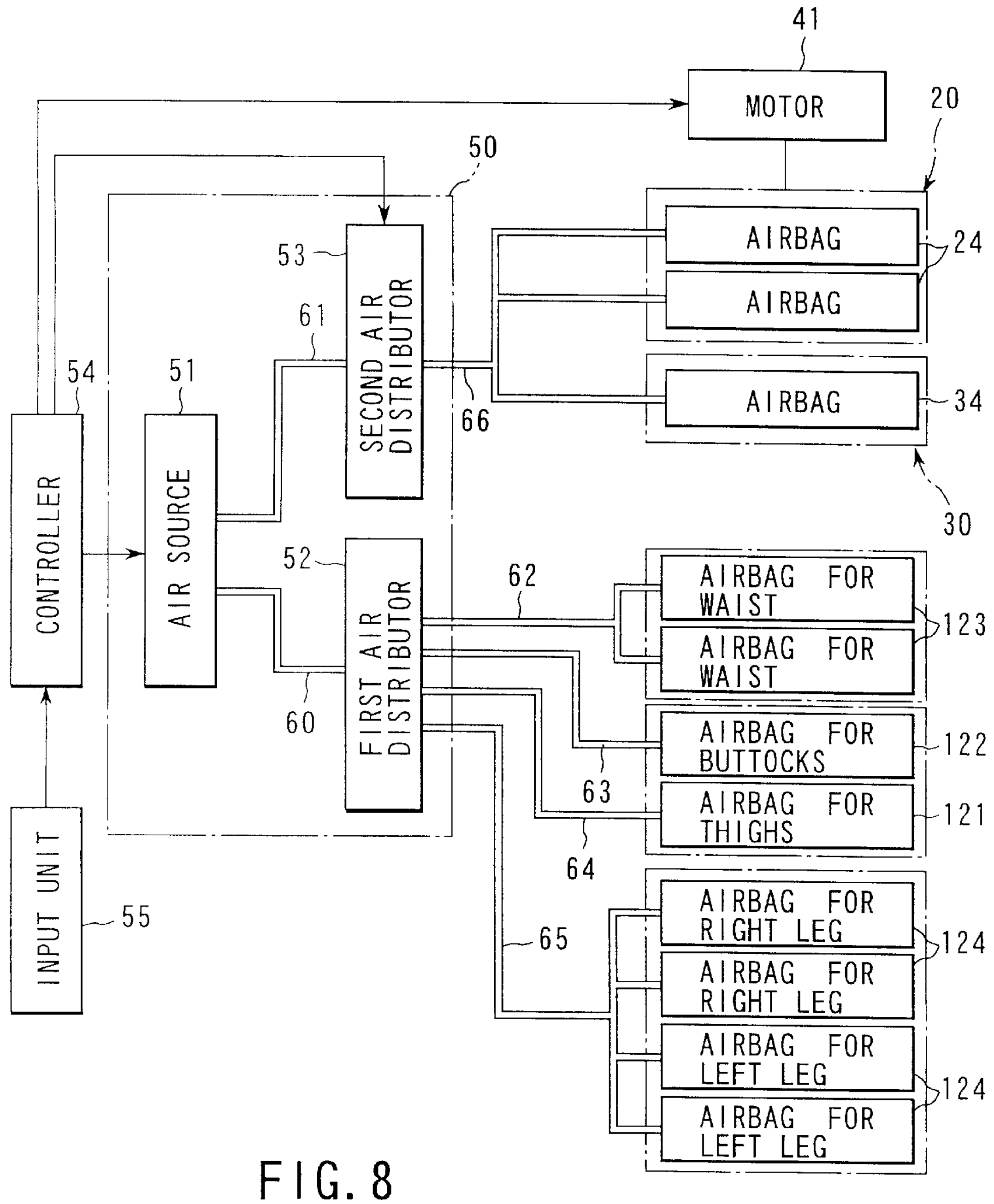
FIG. 8 is a block diagram showing airbags of the massager shown in FIG. 1 and a controller for actuating the airbags.

As shown in FIG. 8, an air hose 62 is connected to the airbags 123 for waist. An air hose 63 is connected to the airbag 122 for buttocks. An air hose 64 is connected to the airbag 121 for thighs. An air hose 65 is connected to the airbags 124 for legs. These air hoses 62 to 65 are connected to the aeration/deaeration device 50. As mentioned later, the device 50 supplies air to the airbags 121 to 124 through their corresponding air hoses 62 to 65. The device 50 can also discharge air in the airbags 121 to 124 through the hoses 62 to 65.

The following is a description of the massage apparatus 1 that is located in the seat back 103.

Figure 2:
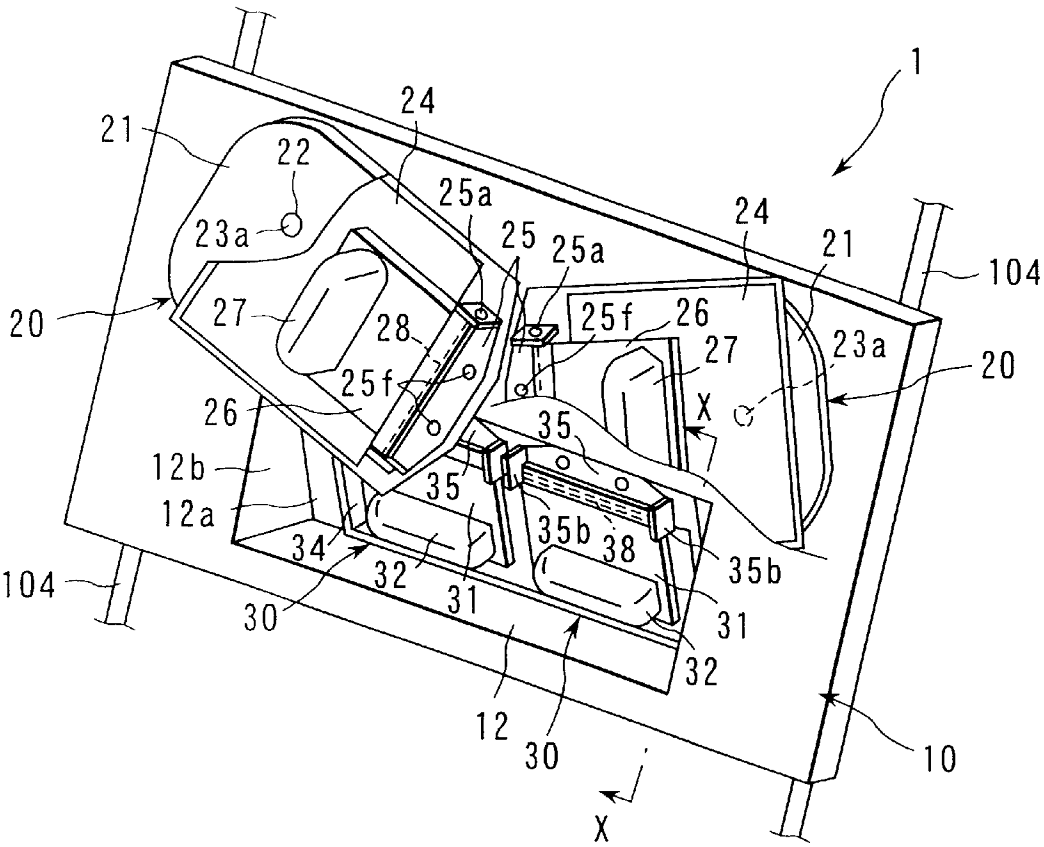
FIG. 2 is a front-side perspective view of a part of the massager shown in FIG. 1.
Figure 3:
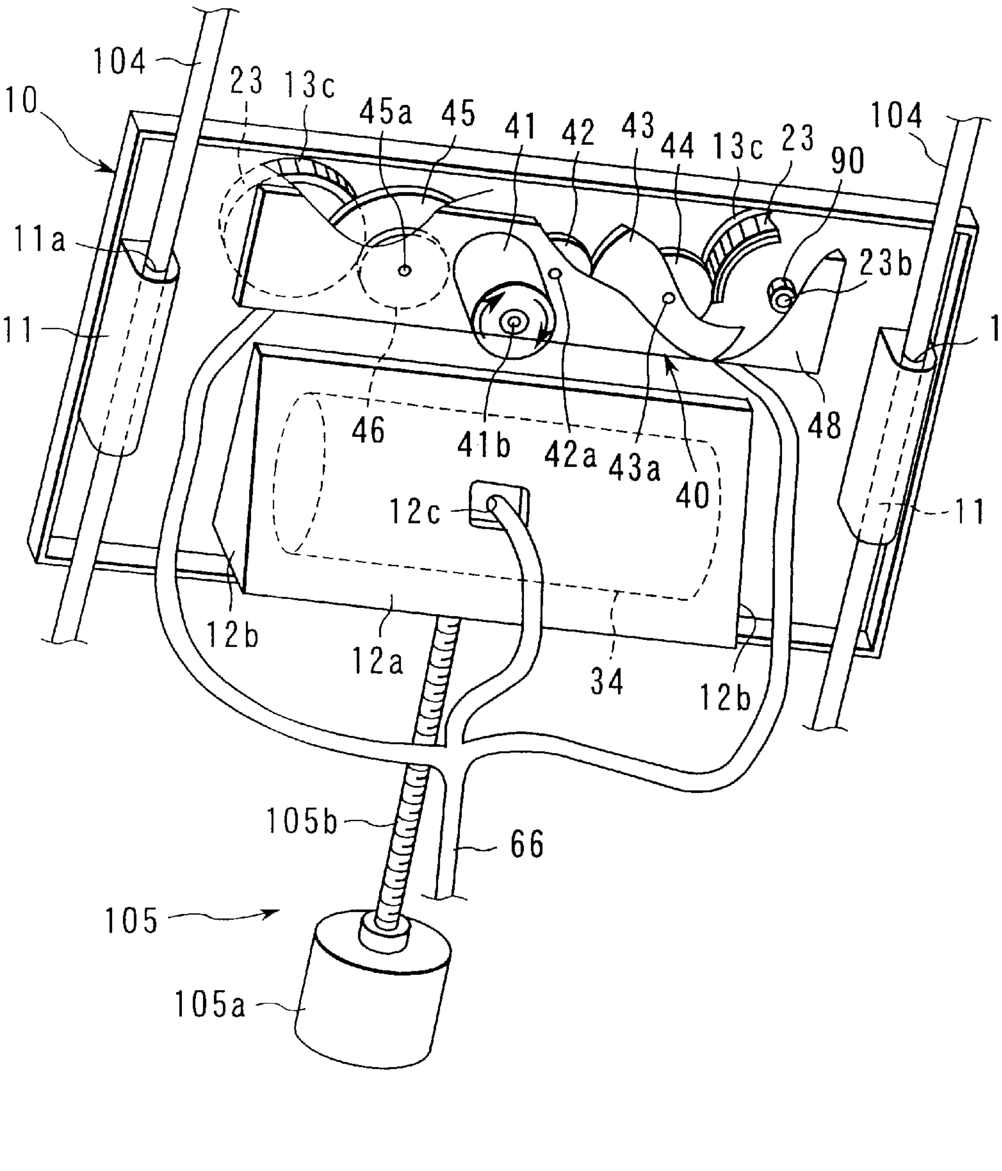
FIG. 3 is a rear-side perspective view of a part of the massager shown in FIG. 1.

As shown in FIG. 2, the massage apparatus 1 comprises a platelike base member 10, a pair of first massage units 20, right and left, mounted on the base member 10, and a pair of second massage units 30, right and left, on the member 10. As shown in FIG. 3, guide members 11 are provided individually on the opposite side portions, right and left, of the base member 10. A guide hole lla vertically extends through each guide member 11. A guide shaft 104 is passed through each guide hole 11*a*. The base member 10 can be moved vertically along the paired guide shafts 104.

In the case of the present embodiment, the base member 10 can be moved to a desired height by means of a lift mechanism 105 that uses a servomotor 105*a* and a feed screw 105*b*. Instead of using the lift mechanism 105, moreover, the base member 10 may be designed so that it can be moved manually in the vertical direction along the guide shafts 104. In this case, braking members such as spring members that are elastically in contact with the guide shafts 104 are arranged individually in the guide holes 11*a* so that the base member 10 can be held at a desired height by means of the braking members.

Figure 5:
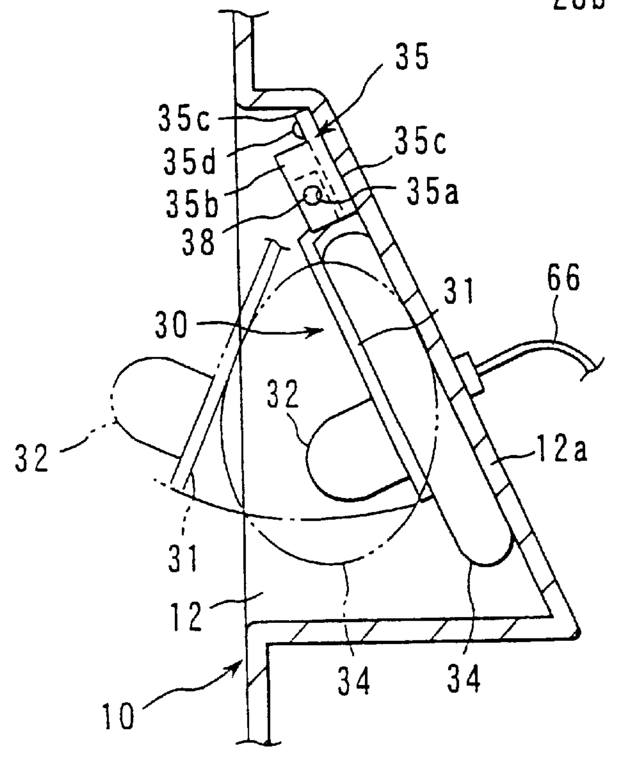
FIG. 5 is a sectional view of a second massage unit taken along line X—X of FIG. 2.

As shown in FIGS. 3 and 5, the lower part of the base member 10 is provided with a slanting wall 12*a* that projects downward and backward and a pair of side walls 12*b* situated individually on the opposite sides of the wall 12*a*. The slanting wall 12*a* and the side walls 12*b* define a recess 12. As shown in FIG. 3, a through hole 12*c* for the passage of an air hose 66 (mentioned later) is formed in the central portion of the slanting wall 12*a*.

Figure 6:
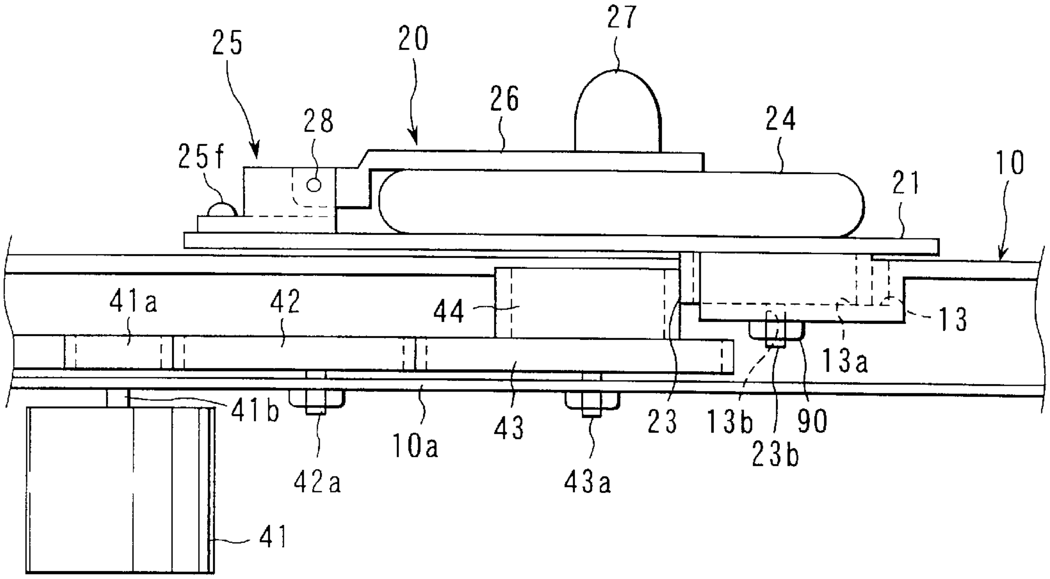
FIG. 6 is a top plan view of a part of the massager shown in FIG. 1.

As shown in FIG. 6, annular recesses 13 (only one of which is illustrated) are formed individually on the opposite sides of upper part of the front face of the base member 10. A bearing hole 13*b* is formed in the central portion of a bottom wall 13*a* of each annular recess 13. As shown in FIG. 3, a through hole 13*c* is formed in a part of the peripheral wall of each recess 13. The hole 13*c* penetrates the base member 10 from top to bottom.

The following is a description of the first massage units 20.

The first massage units 20 comprise a pair of movable elements 21 located for rocking motion in bisymmetrical positions on the base member 10, first tilt members 26 for use as first operating members attached individually to the movable elements 21, first treatment members 27 attached individually to the tilt members 26, airbags 24 for use as actuators for tilting the tilt members 26 in the back-and-forth direction, etc. The paired movable elements 21 are located in bisymmetrical positions on the base member 10. The back-and-forth direction used herein is a direction in which the tilt members 26 move toward or away from a back portion of a user's body to be massaged on the seat cushion 101.

Since the paired movable elements 21 have the same construction, one of the elements 21 will now be described representatively. As shown in FIG. 2, the movable element 21 is in the form of a plate having a shaft hole 22 in one end portion thereof. A pair of gears 23 (shown in FIG. 3) are provided on the reverse surface of the movable elements 21. A shaft 23*a* (shown in FIG. 2) that is rotatable integrally with each gear 23 is inserted in the shaft hole 22. As shown in FIG. 6, the bearing hole 13*b* is formed in the bottom wall 13*a* of the annular recess 13 of the base member 10. A shaft 23*b* that protrudes from the reverse surface of the gear 23 is rockably inserted in the bearing hole 13*b*. The shaft 23*b* is prevented from slipping out of the bearing hole 13*b* by means of a nut 90.

The shaft 23*a* and the shaft hole 22 are fixed to each other in a manner such that a key (not shown) is fitted in a key way (not shown). Thus, the movable element 21 rotates integrally with the gear 23 as the gear 23 rotates around the shaft 23*b*.

Figure 4:
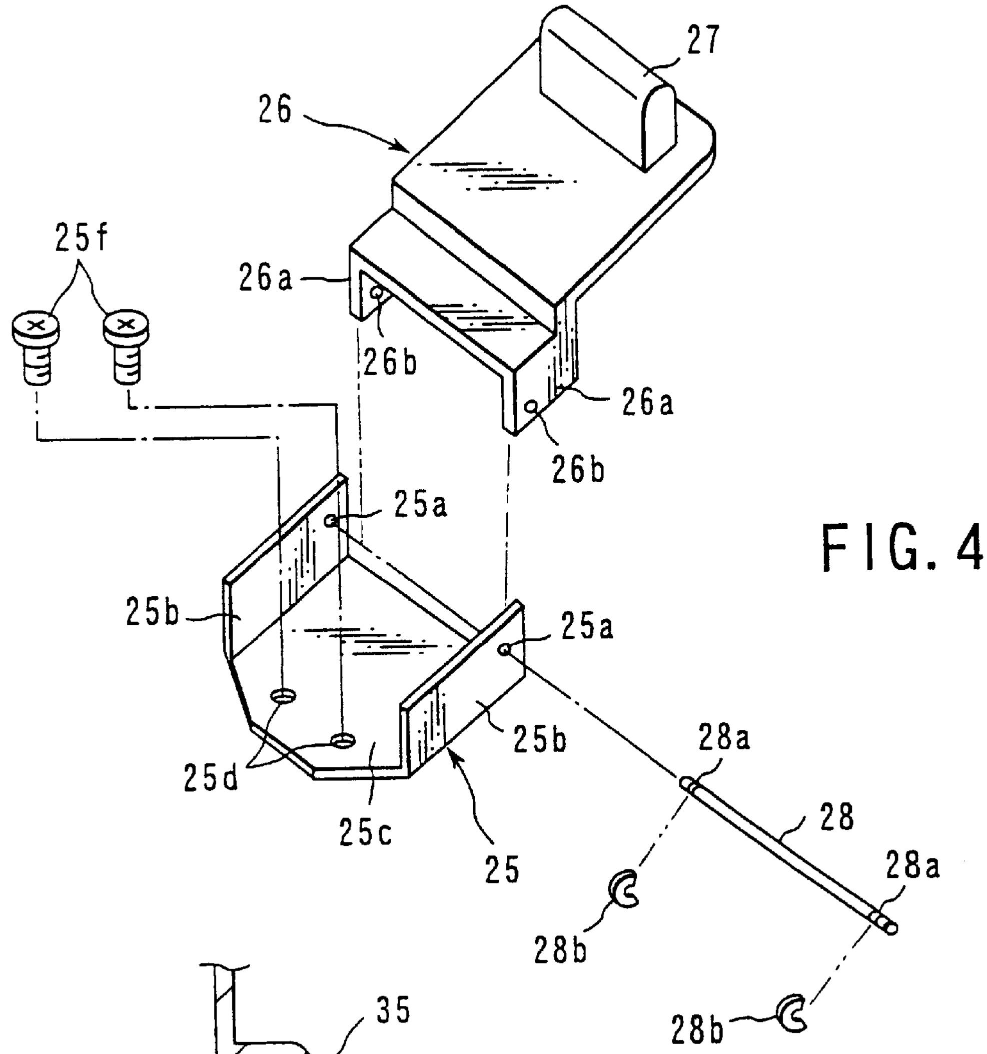
FIG. 4 is an exploded perspective view of a part of a first massage unit of the massager shown in FIG. 1.

A hinge base 25 is mounted on the other end portion of the movable element 21. As shown in FIG. 4, the hinge base 25 includes a bottom wall 25*c*, a pair of side walls 25*b* that rise individually from the opposite sides of the bottom wall 25*c*, and shaft holes 25*a* formed individually in the side walls 25*b*. A shaft 28 is inserted into the paired shaft holes 25*a*. An annular groove 28*a* is formed on each of the opposite ends of the shaft 28. After the shafts 28 are inserted into the shaft holes 25*a,* snap rings 28*b* are fitted individually into the annular grooves 28*a*. The rings 28*b* serve to prevent the shaft 28 from slipping out of the shaft holes 25*a*. The hinge base 25 and the shaft 28 function as first hinge means for rockably supporting the first tilt member 26. Mounting holes 25*d* are formed in the bottom wall 25*c* of the hinge base 25. The hinge base 25 is fixed to the movable element 21 in a manner such that screws 25*f* are inserted individually into the holes 25*d* and fastened to the movable element 21.

As shown in FIG. 4, the tilt member 26 is in the form of a plate. A pair of opposed walls 26*a* are formed on the proximal end portion of the tilt member 26. The walls 26*a* are interposed between the opposite side walls 25*b* of the hinge base 25. Each wall 26*a* is formed having a shaft hole 26*b* in a position corresponding to the shaft hole 25*a* of its corresponding side wall 25*b*. After the shaft 28 is inserted into the shaft holes 25*a* and 26*b,* the snap rings 28*b* are fitted into the annular grooves 28*a,* individually. The first tilt member 26 is rockably supported on the hinge base 25 by means of the shaft 28.

As shown in FIG. 2 or 4, the treatment member 27, substantially semicylindrical, is mounted on an end portion of the first tilt member 26. The treatment member 27 projects forward from the base member 10. The movable element 21 is rockably supported by means of the shaft 23*a,* which is situated above the treatment member 27, so that the member 27 can move along a neck area N1 to a shoulder area N2 of a user's body (shown in FIG. 9A).

The airbag 24 that functions as a first actuator is provided between each movable element 21 and its corresponding tilt member 26. In mounting the airbag 24 on the movable element 21, an edge portion of the airbag 24 is interposed between the movable element 21 and the hinge base 25 as the hinge base 25 is attached to the movable element 21 by means of the screws 25*f,* for example. The screws 25*f* are passed through holes in the edge portion of the airbag 24 and the mounting holes 25*d* of the hinge base 25 and are tightened. By doing this, the edge portion of the airbag 24 can be held between the movable element 21 and the hinge base 25.

The hose 66 is connected to the airbag 24. The hose 66 is used to supply air to the airbag 24. If the airbag 24 is inflated with the air, the tilt member 26 rocks around the shaft 28 and further projects toward the user's body. When air in the airbag 24 is discharged, the airbag 24 deflates, so that the tilt member 26 moves backward or away from the user's body. Thus, the tilt member 26 is activated as the airbag 24 inflates and deflates, whereupon the treatment member 27 presses the user's body as if it performs the finger-pressure treatment.

Springs for urging the tilt member 26 may be provided to move the member 26 away from the user's body as the airbag 24 deflates. Alternatively, the front face of the airbag 24 may be fixed to the reverse surface of the tilt member 26 so that the member 26 can move away from the user's body as the airbag 24 deflates.

Figure 9A:
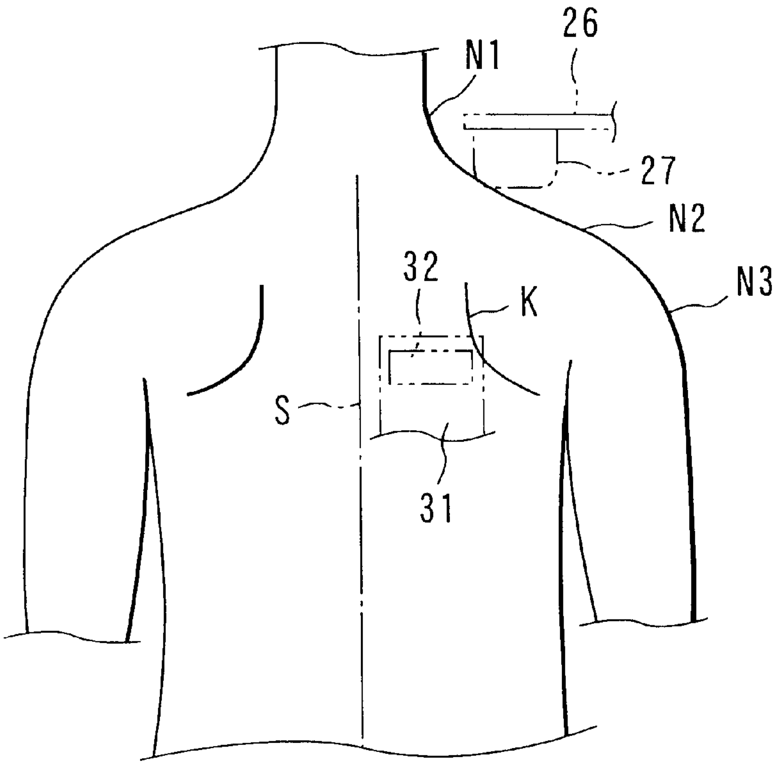
FIG. 9A is a rear view showing positional relations between a user's body and first and second treatment members of the massager shown in FIG. 1.

When the movable element 21 rocks around the shaft 23*a,* the treatment member 27 rocks together with the element 21. As shown in FIG. 9A, the movement of the treatment member 27 that rocks around the shaft 23*a* leaves a trace that resembles a curved line extending from the neck area N1 to the shoulder area N2 of the user's body. In other words, the respective positions of the shaft 23*a* and the treatment member 27 are set so that the path of movement of the member 27 is substantially in line with the curved line that extends from the neck area N1 to the shoulder area N2. Thus, if the movable element 21 rocks as the gear 23 rotates, the treatment member 27 moves leaving a trace that resembles a curved line extending from the nape of the neck area N1 to the top of the shoulder area N2.

The shaft 23*a,* the center of rocking motion of the movable element 21, is situated corresponding to the upper part of the base member 10. On the other hand, the hinge base 25 is situated on the lower part of the movable element 21. If the tilt member 26 is tilted around the shaft 28 by means of the airbag 24 when the treatment member 27 is situated on the nape of the neck area N1, therefore, the treatment member 27 pushes the nape area sideways. If the tilt member 26 is tilted around the shaft 28 by means of the airbag 24 when the treatment member 27 is situated on the shoulder area N2, the treatment member 27 pushes the shoulder area N2 from above.

The following is a description of the second massage units 30.

As shown in FIGS. 2 and 5, the second massage units 30 comprise a pair of second tilt members 31, right and left, which function as second operating members, second treatment members 32 attached individually to the tilt members 31, a second airbag 34 for actuating the tilt members 31, etc. The paired tilt members 31 are located in bisymmetrical positions on the base member 10. These tilt members 31 are attached to the slanting wall 12*a* of the recess 12 of the base member 10. The airbag 34 is interposed between the slanting wall 12*a* and the tilt members 31. In the case of the present embodiment, the one common airbag 34 is located between the slanting wall 12*a* and the paired tilt members 31. Alternatively, however, airbags may be arranged individually between the slanting wall 12*a* and the tilt members 31.

A pair of hinge bases 35 are mounted on the upper part of the slanting wall 12*a*. Each hinge base 35, like the hinge base 25, includes a bottom wall 35*c,* a pair of side walls 35*b* that are formed individually on the opposite sides of the bottom wall 35*c,* and shaft holes 35*a* formed individually in the side walls 35*b*. A shaft 38 is inserted into these shaft holes 35*a*. The shaft 38 is prevented from slipping out of the shaft holes 35*a* in a manner such that snap rings (not shown) are fitted individually into annular grooves that are formed individually the opposite ends of the shaft 38. The hinge base 35 and the shaft 38 function as second hinge means for rockably supporting the upper end portion of the second tilt member 31 on the base member 10. Screws 35*d* are passed individually through mounting holes (not shown) in the bottom wall 35*c* of each hinge base 35 and are fastened to the slanting wall 12*a,* whereby the hinge base 35 is fixed to the wall 12*a*.

As shown in FIG. 2, the upper end portion of each platelike second tilt member 31 is fitted inside the opposite side walls 35*b* of its corresponding hinge base 35. The tilt member 31 is rockably supported on the hinge base 35 by means of the shaft 38 in a position above its corresponding second treatment member 32. More specifically, each tilt member 31 is mounted on the base member 10 so that it can rock toward and away from the user's body around the shaft 38. The treatment member 32, substantially semicylindrical, is mounted on the distal end portion of the tilt member 31.

The airbag 34 is provided between each tilt member 31 and the slanting wall 12*a*. In mounting these airbags 34 on the slanting wall 12*a,* an edge portion of each airbag 34 is interposed between the wall 12*a* and each corresponding hinge base 35 as the hinge base 35 is attached to the wall 12*a* by means of the screws 35*d,* for example. The screws 35*d* are passed through holes in the edge portion of each airbag 34 and the mounting holes of each hinge base 35 and are tightened. By doing this, the respective edge portions of the airbags 34 can be held between the slanting wall 12*a* and the hinge bases 35.

Air is supplied to each airbag 34 through the hose 66. If the airbag 34 is inflated with the air, the tilt member 31 rocks around the shaft 38 and advances toward the user's body. More specifically, the tilt member 31 moves toward the user's body so that the treatment member 32 projects from the recess 12, thereby pressing a back portion (portion between each shoulder blade and the backbone) of the user's body. When air in each airbag 34 is discharged, the airbag 34 deflates, so that the tilt member 31 moves backward or away from the user's body and gets into the recess 12. Thus, the tilt member 31 is activated as the airbag 34 inflates and deflates, whereupon the treatment member 32 presses the user's body as if it performs the finger-pressure treatment.

Springs for urging each tilt member 31 may be provided to move the member 31 away from the user's body as each airbag 34 deflates. Alternatively, the front face of the airbag 34 may be fixed to the reverse surface of the tilt member 31 so that the member 31 can move away from the user's body as the airbag 34 deflates.

When a kneading mode is established by means of an input unit 55 (mentioned later), the airbags 24 and 34 inflate and deflate in synchronism with one another, so that the tilt members 26 and 31 tilt in synchronism with one another. If the airbags 24 and 34 inflate simultaneously, for example, the tilt members 26 and 31 simultaneously tilt forward (toward the user's body).

Since the treatment member 27 on each first tilt member 26 rocks around the first shaft 28, as mentioned before, it presses the shoulder area N2 downward when it is situated the shoulder area N2, as shown in FIG. 9A. Since the treatment member 32 on each second tilt member 31 rocks around the second shaft 38, on the other hand, it presses the region between each shoulder blade K and the backbone S upward. More specifically, the treatment member 32 of each second massage unit 30 presses the region between each shoulder blade K and the backbone S upward as the tilt member 31 tilts around the shaft 38. On the other hand, the treatment member 27 of each first massage unit 20 presses the shoulder area N2 downward.

Figure 9B:
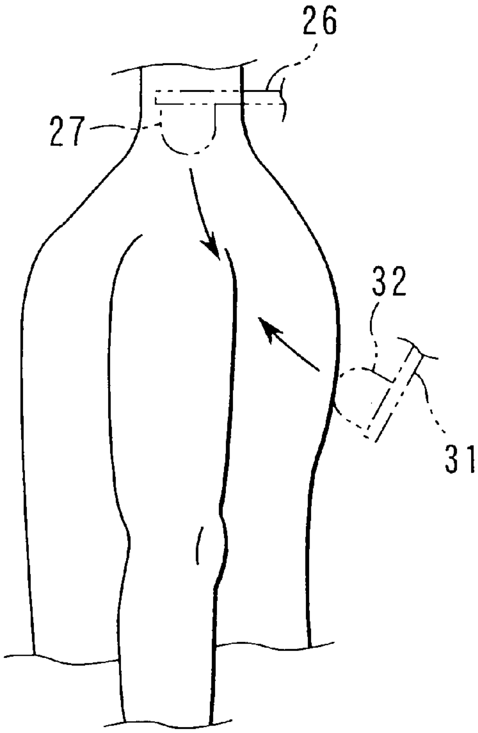
FIG. 9B is a side view showing positional relations between the user's body and the first and second treatment members of the massager shown in FIG. 1.

Thus, a kneading effect can be exerted on the region from the shoulder area N2 to the shoulder blade K as the treatment members 27 and 32 clutch and press the region between the shoulder area N2 and the shoulder blade K, as shown in FIG. 9B. Since each movable element 21 rocks around the shaft 23*a,* moreover, the first treatment member 27 moves in a circular arc from the nape of the neck area N1 to the shoulder area N2 as the second and first treatment members 32 and 27 massage the region from the neck area N1 to the shoulder area N2.

Figure 7:
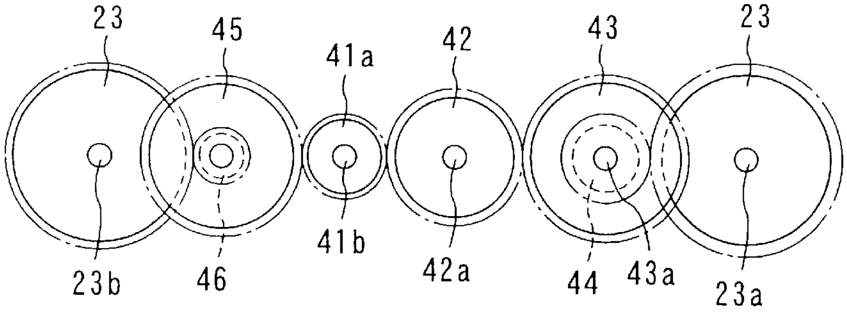
FIG. 7 is a rear view showing a part of a moving mechanism of the massager shown in FIG. 1.

Each first massage unit 20 comprises a moving mechanism 40 for moving the movable element 21 around the shaft 23*a.* The moving mechanism 40 will now be described with reference to FIGS. 3, 6 and 7. The moving mechanism 40 includes a motor 41 such as a stepping motor, a first gear 41*a* mounted on a rotating shaft 41*b* of the motor 41, a second gear 42 in mesh with the first gear 41*a,* a third gear 43 in mesh with the second gear 42, a small-diameter fourth gear 44 integral with the third gear 43, a fifth gear 45 in mesh with the first gear 41*a,* and a sixth gear 46 capable of rotating integrally with the fifth gear 45. The fourth gear 44 is in mesh with the gear 23 that is mounted on the one movable element 21 (on the left-hand side of FIG. 2). The sixth gear 46 is in mesh with the gear 23 that is mounted on the other movable element 21. The number of teeth of each of these gears is adjusted so that the paired movable elements 21 can rotate at the same speed for the same angle without regard to the rotating direction of the rotating shaft 41*b* of the motor 41.

When the rotating shaft 41*b* of the motor 41 rotates in the clockwise direction of FIG. 3, the one movable element 21 rotates in the clockwise direction of FIG. 2, while the other movable element 21 rotates in the counterclockwise direction. Thus, the right- and left-hand first treatment members 27 move along curved surfaces of the user's body that extend from the neck to the right- and left-hand shoulders. When the motor 41 rotates in the counterclockwise direction, the treatment members 27 move in the direction opposite to the aforesaid direction.

The aeration/deaeration device 50 shown in FIG. 8 comprises an air source 51 formed of an air pump or the like, a first air distributor 52 formed of a rotary valve or the like that is connected to the air source 51 by means of one hose 60, and a second air distributor 53 formed of a solenoid valve or the like that is connected to the air source 51 by means of another hose 61. The air source 51 and the distributors 52 and 53 are controlled by means of a controller 54 that includes a microcomputer or the like. The controller 54 also controls the motor 41. Various control signals can be applied to the input of the controller 54 by means of the remote-controlled input unit 55. These control signals include signals for setting various massage modes, starting and stopping the operation of the massager A, etc.

One end of each of the hoses 62 to 65 is connected to the first air distributor 52. The other end of the hose 62 diverges into two branches, which are connected to the paired airbags 123 for waist, individually. The respective other ends of the hoses 63 and 64 are connected to the airbag 122 for buttocks and the airbag 121 for thighs, respectively. The other end of the hose 65 diverges into four branches, which are connected to the airbags 124 for legs, individually. One end of the hose 66 is connected to the second air distributor 53. The other end of the hose 66 diverges into three branches, two of which are connected individually to the airbags 24 of the first massage unit 20, and the remainder to the airbag 34 of the second massage unit 30.

Massage modes that can be established by means of the input unit 55 include, for example, a whole-body massage mode, a bust massage mode, a particular mode, etc. In the whole-body massage mode, the treatment members 27 of the first massage units 20 and the treatment members 32 of the second massage units 30 are activated, and the airbags 123 for waist and the airbags 124 for legs are caused to inflate and deflate in given order for massaging. In the bust massage mode, the treatment members 27 and 32 are activated, and the airbags 123 for waist and the airbag 121 for thighs are caused to inflate and deflate in given order for massaging. In the particular mode, the treatment members 27 of the first massage units 20 and the treatment members 32 of the second massage units 30 operate individually, and the airbags 123 for waist and the airbags 124 for legs individually inflate and deflate in given order to massage various particular parts of the user's body.

In each of these modes, the treatment members 27 of the first massage units 20 and the treatment members 32 of the second massage units 30 operate in the following manner, thereby massaging the nape area, shoulder area, etc.

Let it be supposed that the particular mode is established in the controller 54 by means of the input unit 55 in order to massage the shoulder area N2, for example. In this case, the controller 54 first determines whether or not the motor 41 is in its initial position. When the motor 41 is in its initial position, each movable element 21 is also in its initial position. In this state, each treatment member 27 is situated on the upper part of the nape of the neck area N1. When the motor 41 is not in its initial position, the controller 54 causes the motor 41 to rotate for a given number of steps so that it reaches the initial position, thereby returning the movable element 21 to its initial position.

Then, the controller 54 controls the air source 51 and the second air distributor 53 to start air supply to the airbags 24 of the first massage units 20 and the airbags 34 of the second massage units 30. As the air is supplied in this manner, the airbags 24 and 34 inflate gradually. As these airbags thus inflate, the tilt members 26 and 31 tilt toward the user's body. As the tilt members 26 and 31 move in this manner, the treatment members 27 and 32 clutch and press the nape of the neck area N1 and the back portion. Thus, a finger-pressure effect and a kneading effect are exerted on the nape area and the back portion.

As the airbags 24 and 34 inflate, their internal pressures increase, so that the pressure of air supplied to the airbags 24 and 34 increases gradually. This air pressure is detected by means of a pressure sensor (not shown), and is compared with a control value previously set in the controller 54. If the air pressure is higher than the control value, the controller 54 stops the operation of the air source 51, and controls the second air distributor 53 to deaerate the airbags 24 and 34. By this exhaustion, each first treatment member 27 leaves the nape of the neck area N1, while each second treatment member 32 leaves the back portion and gets into the recess 12.

If the airbags 24 and 34 are deaerated in this manner, the controller 54 causes the motor 41 to rotate for a given number of steps in the clockwise direction of FIG. 3, and then stops the operation of the motor 41. The given number of steps used herein is a value set so that the treatment member 27 can move at given pitches in a region from the neck area N1 to an end portion N3 of the shoulder. As the motor 41 rotates for the given number of steps, the treatment member 27 comes closer to the shoulder area N2 by a given distance from the neck.

Then, the controller 54 controls the air source 51 and the second air distributor 53 again, thereby supplying air to the airbags 24 of the first massage units 20 and the airbags 34 of the second massage units 30. As the air is supplied in this manner, the airbags 24 and 34 inflate gradually. As these airbags thus inflate, the tilt members 26 and 31 move toward the user's body in the same manner as aforesaid. As this is done, the treatment members 27 and 32 clutch and press the region that is nearer to the shoulder area N2 than to the neck area N1 by the given distance from the aforesaid initial position, thereby producing a finger-pressure effect and a kneading effect.

If the pressure of the air supplied to the airbags 24 and 34 is higher than the aforesaid control value, the controller 54 stops the operation of the air source 51, and controls the second air distributor 53 to deaerate the airbags 24 and 34. By this exhaustion, each first treatment member 27 leaves the nape of the neck area N1, while each second treatment member 32 leaves the back portion and gets into the recess 12. Thereafter, the controller 54 drives the motor 41 again for the aforesaid number of steps to move the treatment members 27 and 32 in the same directions as aforesaid. More specifically, the treatment members 27 and 32 come closer to the end portion N3 of the shoulder area N2 by a given distance from the nape area. The controller 54 controls air source 51 and the second air distributor 53 again to inflate the airbags 24 and 34, and thereafter, deaerates the airbags 24 and 34.

The aforesaid series of operations is repeated so that the treatment members 27 and 32 come close to the end portion N3 of the shoulder. After the end portion N3 of the shoulder is nearly reached by the treatment members 27 and 32, the controller 54 causes the motor 41 to rotate reversely. Thus, the treatment members 27 and 32 are moved from positions near the end portion N3 of the shoulder toward the neck area N1. At the same time, the aforesaid control of the air source 51 and the second air distributor 53 is repeated. In consequence, the treatment members 27 and 32 gradually massage regions that center around the back portion and range from the position near the end portion N3 of the shoulder to the neck area N1 in the same manner as aforesaid. Thus, a satisfactory massage effect can be exerted on the regions from the nape area to the end portion N3 of the shoulder.

The massager A, like a conventional air massager, can massage the waist or legs of the user's body in a manner such that the airbags 123 for waist or the airbags 124 for legs are caused to inflate and deflate. In this case, the air source 51 and the first air distributor 52 are controlled by means of controller 54 in the same manner as in the case of the conventional massager, so that a description of this control operation is omitted.

As mentioned before, the massage apparatus 1 that is located in the seat back 103 of the chair body 100 is provided with the pair of first massage units 20, right and left, and the pair of second massage units 30, right and left. The seat back 103 is provided with the guide shafts 104 that extend vertically. The first and second massage units 20 and 30 can be moved along the guide shafts 104 to desired heights.

The first massage units 20 comprise the base member 10 mounted on the guide shafts 104, movable elements 21 located on the base member 10 for rocking motion around the shafts 23*a,* first tilt members 26 attached individually to the movable elements 21 by means of the hinge bases 25 and the shafts 28, first treatment members 27 provided individually on the tilt members 26, first airbags 24 for actuating the tilt members 26, etc. The base member 10 is provided with the paired hinge bases 25 that are located individually in bisymmetrical positions under their corresponding shafts 23*a*.

The second massage units 30 comprise the second tilt members 31, second treatment members 32 attached individually to the tilt members 31, second airbag 34 for actuating the tilt members 31, etc. The upper part of each second tilt member 31 is rockably supported on the base member 10 by means of the hinge base 35 and the shaft 38. The first treatment members 27 are activated by causing the first airbags 24 to inflate or deflate, while the second treatment members 32 are activated by causing the second airbags 34 to inflate or deflate. This massage apparatus 1 partially holds the user's body by bringing the first treatment members 27 on the first tilt members 26 and the second treatment members 32 on the second tilt members 31 close to one another, so that it can exert a kneading effect on the user's body.

Further, each first treatment member 27 can be moved along a curved surface of the user's body that extends from the nape of the neck area N1 to the shoulder area N2 in a manner such that the movable element 21 of each first massage unit 20 is rocked around the shaft 23*a*. Accordingly, the first treatment member 27 presses the top surface of the user's body that extends from the nape area to a position near the end portion N3 of the shoulder, and the second treatment member 32 presses the back portion. Thus, the region between the shoulder area N2 and the back portion can be held between the treatment members 27 and 32, and a kneading effect can be exerted on the regions that center around the back portion and range from the nape area to the position near the end portion N3 of the shoulder. In consequence, a very good massage effect can be obtained.

The first treatment member 27 on the movable element 21 of each first massage unit 20 is provided near the distal end of the tilt member 26 that is rockable around the shaft 28 so that it can tilt toward the user's body. The proximal end portion of the tilt member 26 is mounted on the movable element 21 by means of the shaft 28. The tilt member 26 is designed so as to be tilted around the shaft 28 by means of the airbag 24 that is located between the movable element 21 and the tilt member 26. Thus, the mechanism for tilting the tilt member 26 is simple.

Since the movable element 21 of each first massage unit 20 rocks around the shaft 23*a*, the first treatment member 27 can be moved along the curved surface that ranges from the neck area N1 to the shoulder area N2 with use of a simple construction.

The treatment members 27 of the first massage units 20 normally project forward from the base member 10. On the other hand, the treatment members 32 of the second massage units 30 are located in positions such that they can press the back portion of the user's body, and can be held in the recess 12 of the base member 10 when not in operation. Therefore, the user to be massaged can easily notice the presence of the projecting treatment members 27 of the first massage units 20 from outside the cover member K1. Accordingly, the positions of the treatment members 27 can be easily adjusted by, for example, operating the lift mechanism 105 so that the treatment members 27 can massage desired regions such as the region from the nape area to the shoulder area N2. During this positioning operation, the treatment members 32 of the second massage units 30 are held in the recess 12 and cannot abut the back portion, so that they never hinder the position adjustment for the treatment members 27.

Since the massage apparatus 1 is located in the chair body 100, the user can sit relaxed on the seat cushion 101 when he/she is massaged. In this embodiment, the massage apparatus 1 is incorporated in the chair body 100. Alternatively, however, the massage apparatus 1 may be incorporated in a flat support member, such as a mattress or bed.

According to the embodiment described above, the treatment member 27 of each first massage unit 20 is designed repeatedly to press and release the region from the nape area to the shoulder area N2 by inflating and deflating the airbag 24. Instead of repeatedly pressing and releasing the region, however, the movable element 21 may be rotated around the shaft 23*a* with the airbag 24 inflated or with the treatment member 27 kept projecting toward the user's body. By doing this, the treatment member 27 can be made to move pressing the region from the neck area N1 to the shoulder area N2, so that it can produce a rubbing effect. In this case, the movable element 21 also rocks around the shaft 23*a*, so that the treatment member 27 can be smoothly moved from the neck area N1 to the position near the end portion N3 of the shoulder. In the embodiment shown in FIG. 8, the airbags 24 of the first massage units 20 and the airbag 34 of the second massage units 30 are driven by means of the one distributor 53. Alternatively, the airbags 24 and 34 can be operated independently of one another if separate distributors are used to drive them.

In the massager A of the embodiment described above, each treatment member 27 is moved along the curved surface that ranges from the neck area N1 to the shoulder area N2 in a manner such that the movable element 21 is rocked around the shaft 23*a*. Alternatively, each movable element may be moved along a curved guide groove on the base member 10 that is formed extending along the curved surface from the neck area N1 to the shoulder area N2. In this case also, the movable element is provided with the tilt member 26 having the treatment member 27 thereon and the airbag 24 for activating the tilt member 26.

In the massager A of the foregoing, embodiment, the airbags 24 are used as actuators for actuating the tilt members 26. Alternatively, the tilt members 26 may be designed to be tilted by means of mechanical means such as a cam that is rotated by means of a motor. Further, the platelike tilt members 26 may be replaced with strip- or rod-shaped tilt members. Each treatment member 27 is not limited to the semicylindrical shape, and may alternatively be a protrusion having a hemispherical distal end portion.

The massager A of the foregoing embodiment is provided with the first second massage units 20 and 30. However, the present invention is also applicable to a massager that is provided with the first massage units 20 only. Further, a rubbing massage may be carried out by inflating the airbags 24 and moving the region from the nape area to the shoulder area with the treatment members 27 kept projecting toward the user's body. In the case where the treatment members 27 are used to give the rubbing massage only, they may be provided directly on the movable elements 21 without using the tilt members 26 and the airbags 24.

In the massager A, each movable element 21 is driven so that the treatment member 27 can move along the curved surface that ranges from the neck area N1 to the shoulder area N2. Alternatively, each treatment member 27 may be designed so as to be movable along any other region of the user's body than the aforesaid curved surface. Further, the second massage units 30 may be constructed so as to be movable in the vertical or horizontal direction with respect to the base member 10.

The massager A is provided with the first air distributor 52 in order to aerate and deaerate the airbags 123 for waist or the airbags 124 for legs in the chair body 100. In the case of a massager that uses neither the airbags 123 for waist nor the airbags 124 for legs, the first air distributor 52 can be omitted.

Figure 10:
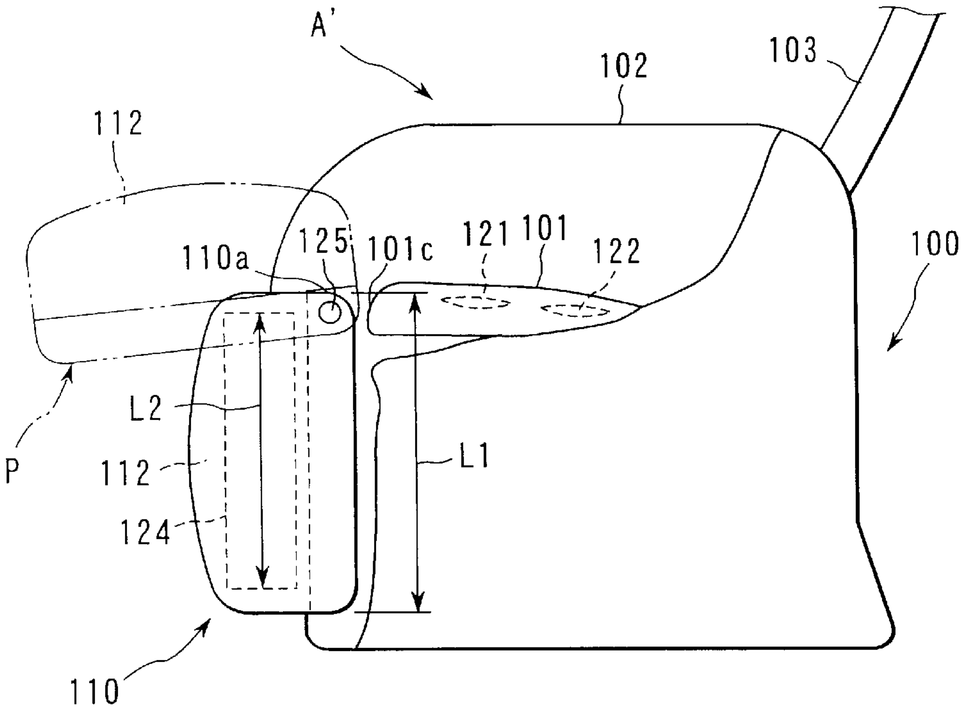
FIG. 10 is a side view of a part of a massager according to a second embodiment of the invention.
Figure 11:
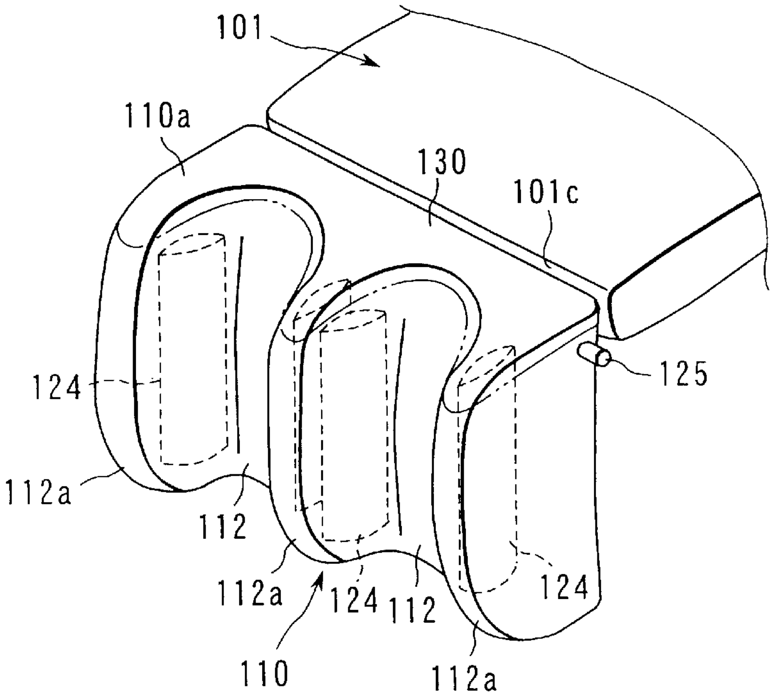
FIG. 11 is a perspective view of a part of the massager shown in FIG. 10.

FIGS. 10 and 11 show a massager A' according to a second embodiment of the invention. The massager A', like the massager A, is provided with a footrest 110 that is vertically rockable around a shaft 125. If the user's legs are fitted individually in grooves 112 of the footrest 110 that is raised to a substantially horizontal position, as indicated by two-dot chain line P in FIG. 10, they can be massaged by means of airbags 124.

In this footrest 110, the shaft 125 is located near an upper end edge 101*c* of the front part of seat cushion 101 so that a rear end face 110*a* of the footrest 110 is substantially flush with the upper surface of the seat cushion 101 when the footrest 110 is rocked down around the shaft 125, as shown in FIG. 11. According to this embodiment, a length L1 of the footrest 110 can be made greater than that of a conventional massager in which the rear end face 110*a* of the footrest 110 is situated considerably lower than the upper surface of the seat cushion 101. Therefore, the grooves 112 in which the legs are to be fitted as they are massaged can be made long. Thus, the airbags 124 with a length L2 great enough to massage the entire legs satisfactorily can be stored in the footrest 110.

As shown in FIG. 11, a cushion member 130 is provided on the rear end face 110*a* of the footrest 110. In this case, the legs on the footrest 110 are in contact with the cushion member 130. If the rear end face 110*a* of the footrest 110 is on the same level as the upper surface of the seat cushion 101, therefore, the comfortableness to sit on the massager cannot be ruined. For other configurations and effects, the massager A' of the present embodiment is similar to the massager A of the first embodiment. Thus, common numerals are used to designate those portions which are common to the two massagers, and a description of those portions is omitted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A massager comprising:

a support member including a seat back;

a base member provided in the seat back and including a front face located along the seat back; and right and left massage units arranged on the base member;

wherein each of the right and left massage units includes:

a rotational-center member;

a movable element supported by the rotational-center member such that the movable element is rotatable along the front face of the base member;

a rotating mechanism including a motor and a power transmission system for rotating the movable body around the rotational-center member;

a treatment member that is coupled to the movable element and that is adapted to be moved in an arc shape along the front face of the base member when the movable element is rotated around the rotational-center member; and a pushing device for pushing the treatment member into the seat back.

2. A massager according to claim 1, wherein the pushing device comprises:

an operating member located on the movable element and coupled to the treatment member;

a supporting device for supporting a proximal portion of the operating member so that the treatment member can be moved into and away from the seat back; and an actuator located between the movable element and the operating member and adapted to inflate or deflate when air is supplied thereto or discharged therefrom.

3. A massager according to claim 2, further comprising an additional massage unit arranged on the base member below the right and left message units, said additional massage unit including:

an additional operating member provided on the base member;

an additional treatment member provided on the additional operating member;

an additional supporting device for supporting an upper end portion of the additional operating member so that a lower end portion of the additional operating member can be moved back and forth; and an additional actuator for moving the additional operating member forward with respect to the base member.

4. A massager according to claim 3, wherein a recess is formed in the base member, and the additional treatment member is adapted to be retreated into and held in said recess.

5. A massager according to claim 1, wherein said to support member comprises a support body including said seat back and a seat cushion.

6. A massager according to claim 5, wherein said seat back is provided with a lift mechanism for vertically moving the base member.

* * * * *

UNITED STATES PATENT AND TRADEMARK OFFICE

CERTIFICATE OF CORRECTION

PATENT NO. : 6,517,500 B2
DATED : February 11, 2003
INVENTOR(S) : Hiromitsu Ichikawa It is certified that error appears in the above-identified patent and that said Letters Patent is hereby corrected as shown below:

Title page,
Item [73], Assignee, change "Tech" to -- Tec --.

Signed and Sealed this

Ninth Day of September, 2003

JAMES E. ROGAN
*Director of the United States Patent and Trademark Office*